United States Patent [19]

Meek et al.

[11] Plant 4,960

[45] Nov. 30, 1982

[54] CHRYSANTHEMUM PLANT

[75] Inventors: Jack M. Meek; William E. Duffett, both of Salinas, Calif.

[73] Assignee: Yoder Brothers, Inc., Barberton, Ohio

[21] Appl. No.: 160,815

[22] Filed: Jun. 18, 1980

[51] Int. Cl.[3] ..... A01H 5/00

[52] U.S. Cl. ..... Plt./76

[58] Field of Search ..... Plt./76

*Primary Examiner*—James R. Feyrer

*Attorney, Agent, or Firm*—Schwartz, Jeffery, Schwaab, Mack, Blumenthal & Koch

[57] ABSTRACT

A chrysanthemum plant known by the cultivar name Luv and particularly characterized as to uniqueness by the combined characteristics of flat capitulum form; decorative capitulum type; lavender pink ray floret color; diameter across face of capitulum ranging from 105 to 115 mm. at maturity; uniform eight week photoperiodic flowering response to short days; short plant height when grown as a pinched disbud pot; and semi-spreading branching pattern.

3 Drawing Figures

1

The present invention comprises a new and distinct cultivar of *Chrysanthemum morifolium,* Ramat., hereinafter referred to by the cultivar name Luv.

Luv is a product of a planned breeding program which had the objective of creating new chrysanthemum cultivars having decorative capitulum type, lavender ray floret color, eight week flowering response, and having the ability to produce commercially acceptable quality in year round pot mum programs. Such traits in combination were not present in previously available commercial cultivars.

Luv was originated from a cross made in a controlled breeding program in Salinas, Calif. in 1977. The female parent was Tempo, disclosed in U.S. Plant Pat. No. 4,505, granted Feb. 26, 1980. The male parent of Luv was an unnamed pink incurved seedling (#70029014) originated from a hybridization of Snowpink (unpatented; commercially available) and Pamplemousse (unpatented; commercially available).

Luv was discovered and selected as one flowering plant within the progeny of the stated cross by William E. Duffett on Feb. 28, 1978 in a controlled environment in Salinas, Calif.

The first act of asexual reproduction of Luv was accomplished when vegetative cuttings were taken from the initial selection in April, 1978 in a controlled environment in Salinas, Calif. by a technician working under formulations established and supervised by Jack M. Meek. Horticultural examination of selected units initiated Nov. 27, 1978 has demonstrated that the combination of characteristics as herein disclosed for Luv are firmly fixed and are retained through successive generations of asexual reproduction.

Luv has not been observed under all possible environmental conditions. The phenotype may vary significantly with variations in environment such as temperature, light intensity, and day length. The following observations, measurements, and comparisons describe plants grown in Salinas, Calif. under greenhouse conditions which approximate those generally used in commercial practice.

The following traits have been repeatedly observed and are determined to be basic characteristics of Luv which in combination distinguish this chrysanthemum as a new and distinct cultivar:

2

(1) Flat capitulum form;
(2) Decorative capitulum type;
(3) Lavender pink ray floret color, with minimal color oxidation;
(4) Diameter across face of capitulum ranging from 105 to 115 mm. at maturity;
(5) Uniform eight week photoperiodic flowering response to short days;
(6) Short plant height (requiring 2–3 long day weeks prior to pinch and short days, and one application 2500 ppm B-9 SP 14 to 21 days after the beginning of short days to attain a flowered plant height of 30 to 45 cm.); and
(7) Semi-spreading branching pattern.

The accompanying photographic drawings show typical inflorescence and foliage characteristics of Luv. Sheet 1 is a color photograph showing four (4) plants in a 6 inch pot. Some difficulty was encountered in obtaining true photographic color representation. Sheet 2 is a black and white photograph showing three views of the inflorescence of Luv. Sheet 3 is a black and white photograph of the foliage of Luv at three stages of growth.

Of the many commercial cultivars known to the present inventors, the most similar in comparison to Luv is Always Pink, disclosed in U.S. Plant Pat. No. 3,256. Reference is made to attached Chart A which compares certain characteristics of Luv to those same characteristics of Always Pink. When generally compared to Always Pink, Luv has different ray floret color and larger diameter across face of capitulum. The capitulum form, capitulum type, branching pattern, plant height, and flowering response period of Luv are similar to those same characteristics of Always Pink.

In the following description, color references are made to A Limit Color Cascade by the Munsell Company, 1972 edition. The color values were determined between 8:30 and 9:00 A.M. on Mar. 28, 1980, under 125 foot-candle light intensity at Salinas, Calif., Classification:

*Botanical.*—*Chrysanthemum morifolium,* Ramat., cv Luv.

*Commercial.*—Pinched decorative disbud pot.

I. Inflorescence:

A. *Capitulum*—Form: Flat. Type: Decorative. Diameter across face: 105 to 115 mm.

B. *Corolla of ray florets.*—General tonality from a distance of 3 meters: 46-6 to 45-4. Color (abaxial): Approximately 46-5 streaked with 46-7, oxidizing to 46-4 streaked with 46-6. Color (adaxial): approximately 46-4 streaked with 46-6. Persistence: Resists shatter.

C. *Reproductive organs.*—Androecium: Present disc florets only; scant to few; scant pollen. Gynoecium: Present both ray and disc florets.

II. Plant:

A. *General appearance.*—Height: Short. Branching pattern: Semi-spreading.

B. *Foliage.*—Color (abaxial): Approximately 20-15. Color (adaxial): Approximately 20–15 overlaid with white. Shape: Moderately lobed and slightly serrated.

CHART A

COMPARISON OF LUV AND ALWAYS PINK

| CULTIVAR | RAY FLORET COLOR | CAPITULUM FORM AND TYPE | BRANCHING PATTERN |
|---|---|---|---|
| LUV | Lavender | Flat | Semi- |

CHART A-continued

COMPARISON OF LUV AND ALWAYS PINK

| | | | |
|---|---|---|---|
| ALWAYS PINK | Pink<br>Dark Lavender to Lavender | Decorative<br>Falt Decorative | spreading<br>Semi-spreading |

| CULTIVAR | DIAMETER ACROSS FACE OF CAPITULUM | PLANT HEIGHT | FLOWERING RESPONSE PERIOD |
|---|---|---|---|
| LUV | 105 to 115 mm. | Short | 8 week |
| ALWAYS PINK | 85 to 95 mm. | Short | 8 week |

COMPARISONS MADE OF PLANTS GROWN AS PINCHED DISBUDDED POTS IN SALINAS, CALIFORNIA.

We claim:

1. A new and distinct cultivar of *Chrysanthemum morifolium,* Ramat., plant known by the cultivar name of Luv, as described and illustrated, and particularly characterized as to uniqueness by the combined characteristics of flat capitulum form; decorative capitulum type; lavender pink ray floret color, with minimal color oxidation; diameter across face of capitulum ranging from 105 to 115 mm. at maturity; uniform eight week flowering response; short plant height; and semi-spreading branching pattern.

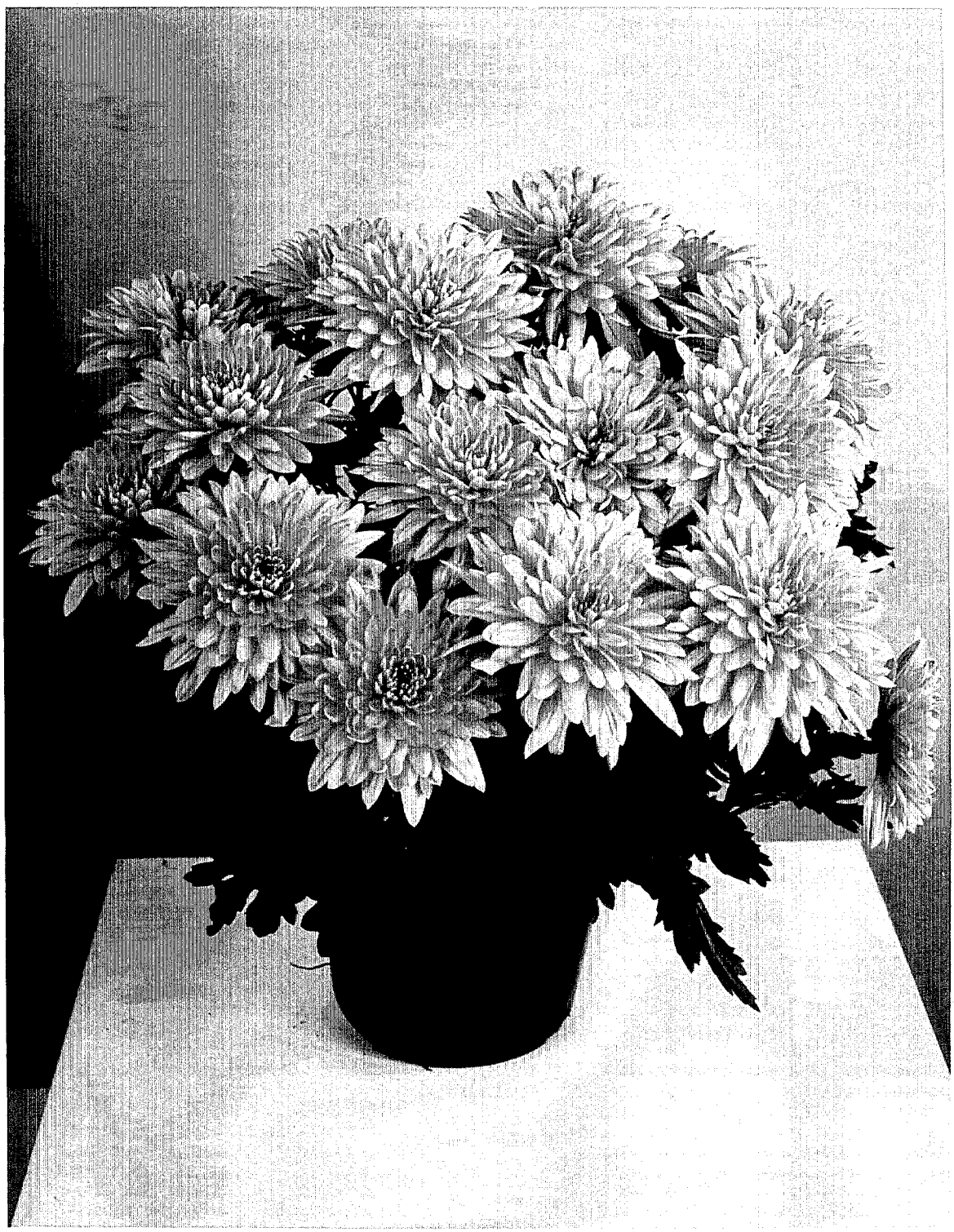

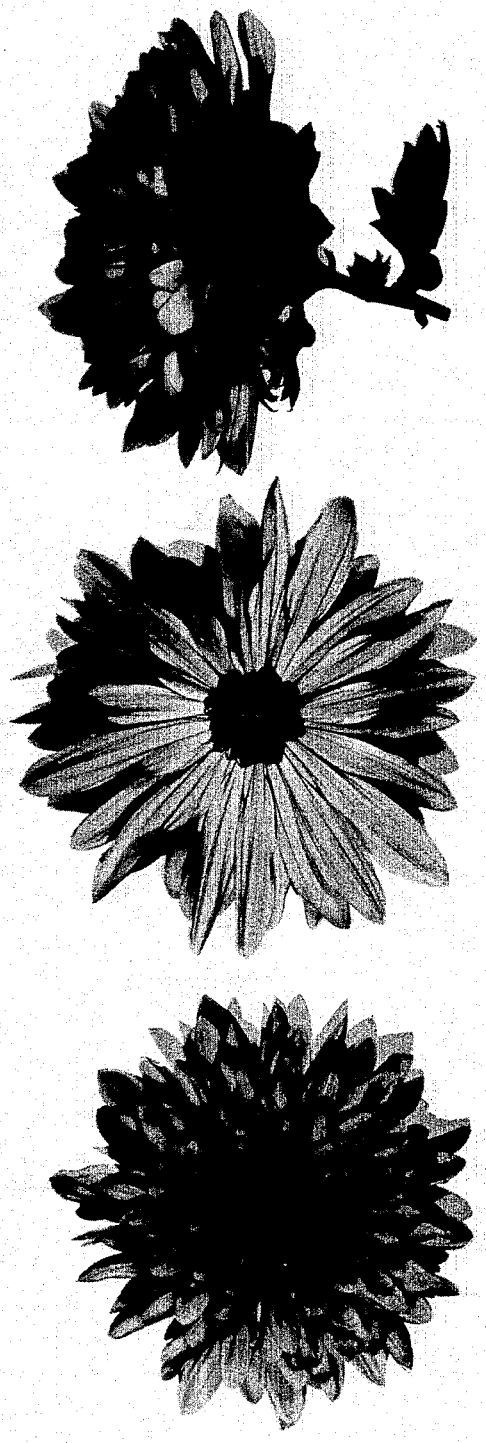

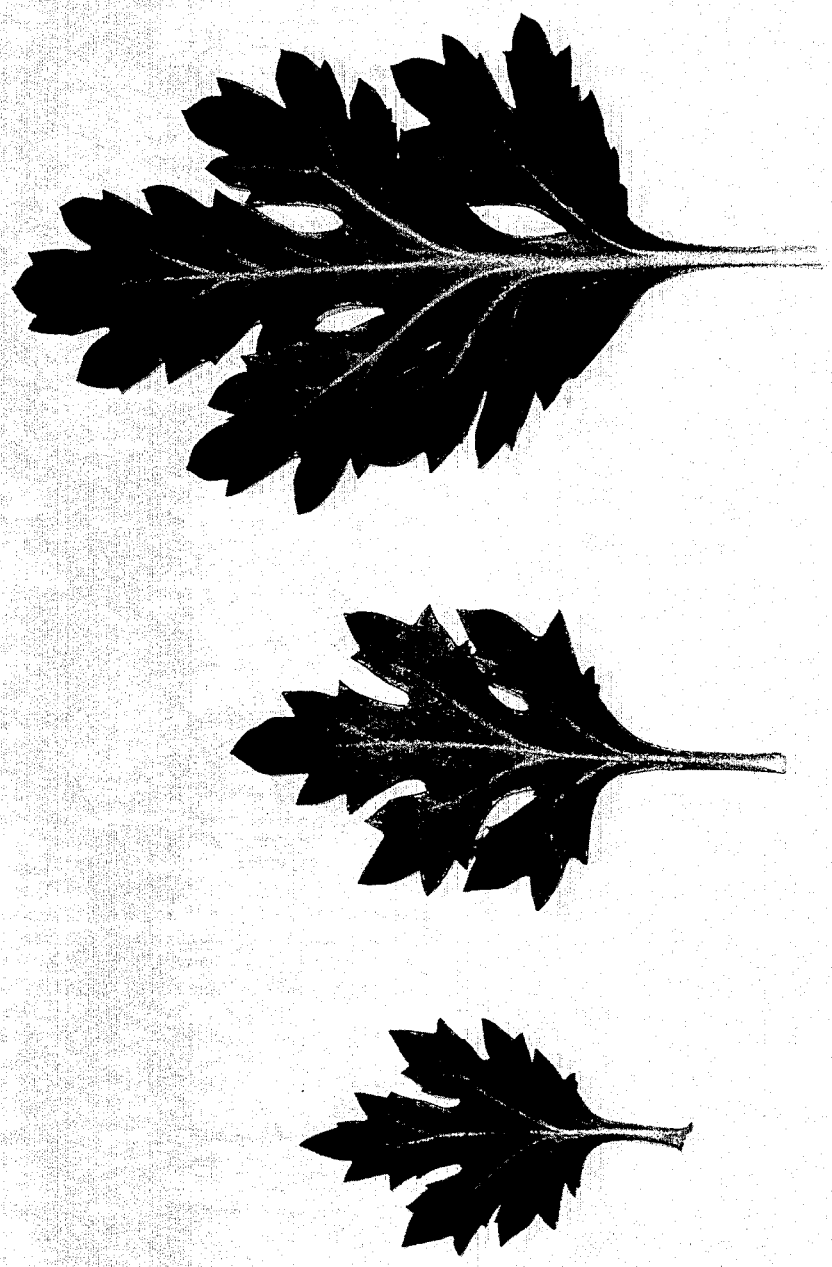

* * * * *